United States Patent [19]

Alpegiani et al.

[11] Patent Number: 5,585,372
[45] Date of Patent: Dec. 17, 1996

[54] TRICYCLIC CEFEM SULPHONES

[75] Inventors: Marco Alpegiani, Milan; Pierluigi Bissolino, San Giorgio di Lomellina; Ettore Perrone, Boffalora Ticino; Vincenzo Rizzo, Arese, all of Italy

[73] Assignee: Pharmacia S.p.A., Milan, Italy

[21] Appl. No.: 367,319

[22] PCT Filed: May 17, 1994

[86] PCT No.: PCT/EP94/01643

§ 371 Date: Jan. 20, 1995

§ 102(e) Date: Jan. 20, 1995

[87] PCT Pub. No.: WO94/28003

PCT Pub. Date: Dec. 8, 1994

[30] Foreign Application Priority Data

May 20, 1993 [GB] United Kingdom .................. 9310428

[51] Int. Cl.$^6$ .................. C07D 501/62; A61K 31/545
[52] U.S. Cl. .................. 514/200; 514/202; 514/208; 540/216
[58] Field of Search .................. 540/215, 221, 540/222, 216; 514/202, 200, 204

[56] References Cited

U.S. PATENT DOCUMENTS 4,547,371 10/1985 Doherty et al. .................. 514/200

OTHER PUBLICATIONS

Beeby et al, Tetrahedron Letters No. 37 pp. 3261–3264 (1976).

*Primary Examiner*—John M. Ford
*Attorney, Agent, or Firm*—Oblon, Spivak, McClelland, Maier & Neustadt, P.C.

[57] ABSTRACT

The present invention provides compounds of formula (I) and pharmaceutically or veterinarily salts thereof;

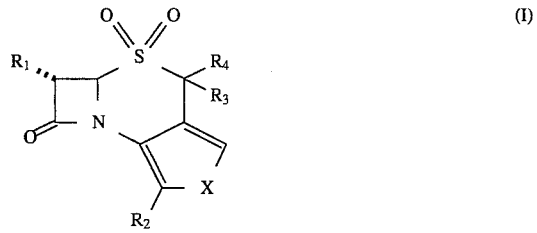

wherein $R_1$ is hydrogen or halogen or an organic group;

$R_2$ is hydrogen or an optionally substituted $C_1$–$C_6$ alkyl, $C_3$–$C_6$ cycloalkyl, $C_6$–$C_{10}$ aryl or $C_7$–$C_{14}$ aralkyl group;

$R_3$ is hydrogen or halogen, or an organic group $R_4$ is hydrogen or a group defined as $R_2$ above or $R_4$ taken together with $R_3$ constitutes a $C_2$–$C_6$ alkanediyl or an alkanediyl radical optionally substituted by methyl or phenyl and X is either oxygen or sulphur or $NR_6$, wherein $R_6$ is either hydrogen or a group as defined for $R_2$. A process for their preparation by cyclization of appropriate intermediates is also described.

The compounds of formula I and the pharmaceutically and veterinarily acceptable salts thereof are elastase inhibitors.

12 Claims, No Drawings

TRICYCLIC CEFEM SULPHONES

This is a 371 of PCT/EP94/01643, filed 17 May 1994.

The present invention relates to new cephalosporin sulphones, their preparation and to pharmaceutical and veterinary compositions containing them. The compounds disclosed in the present invention are tricyclic β-lactam derivatives characterized by a cephem sulfone skeleton fused with a furane, thiophene or pyrrole ring. According to the invention there are provided compounds of formula (I) and the pharmaceutically and veterinarily acceptable salt thereof:

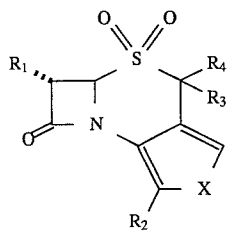

wherein $R_1$ is hydrogen or halogen or an optionally substituted $C_1$–$C_6$ alkyl, $C_2$–$C_6$ alkenyl, $C_1$–$C_6$ alkoxy, $C_1$–$C_6$ alkylthio, $C_1$–$C_6$ acyloxy or $C_1$–$C_6$ carboxamido group;

$R_2$ is hydrogen or an optionally substituted $C_1$–$C_6$ alkyl, $C_3$–$C_6$ cycloalkyl, $C_6$–$C_{10}$ aryl or $C_7$–$C_{14}$ aralkyl group;

$R_3$ is hydrogen or halogen or an optionally substituted $C_1$–$C_6$ alkyl, $C_3$–$C_6$ cycloalkyl, $C_7$–$C_{14}$ aralkyl group or an optionally substituted —$(CH_2)_m S(O)_n R_5$ group wherein m is 0 or 1, n is 0, 1 or 2 and $R_5$ is either a group defined as $R_2$ above or an optionally substituted heterocyclyl group; or a group of the formula OCOA, wherein A is hydrogen or an optionally substituted $C_1$–$C_{10}$ alkyl, $C_3$–$C_6$ cycloalkyl, $C_6$–$C_{10}$ aryl or $C_{7-14}$ aralkyl or heterocyclyl group, $R_4$ is hydrogen or a group defined as $R_2$ above or $R_4$ taken together with $R_3$ constitutes a $C_2$–$C_6$ alkanediyl or an alkanediyl radical optionally substituted by methyl or phenyl, and X is either oxygen or sulphur or $NR_6$, wherein $R_6$ is either hydrogen or a group as defined for $R_2$.

The term halogen preferably encompasses fluorine, chlorine or bromine.

The $C_1$–$C_6$ alkyl group is a straight or branched alkyl group such as methyl, ethyl, n-propyl, isopropyl, n-butyl, isobutyl, sec-butyl, tert-butyl, n-pentyl, n-hexyl and so on.

The $C_2$–$C_6$ alkenyl group is a straight or branched alkenyl group such as vinyl, allyl, crotyl, 2-methyl-1-propenyl, 1-methyl-1-propenyl, butenyl, pentenyl and so on.

The $C_1$–$C_6$ alkoxy group is a straight or branched alkoxy group such as methoxy, ethoxy, n-propoxy, isopropoxy, n-butoxy, isobutoxy, sec-butoxy, tert-butoxy, n-pentoxy, n-hexyloxy and so on.

The $C_1$–$C_6$ alkylthio group is a straight or branched alkylthio group such as methylthio, ethylthio, n-propylthio, isopropylthio, n-butylthio, isobutylthio, sec-butylthio, tert-butylthio, n-pentylthio, n-hexylthio and so on.

The $C_1$–$C_6$ acyloxy group is a straight or branched carboxylic acyloxy such as formyloxy, acetoxy, propionyloxy, butyryloxy, isobutyryloxy, valeryloxy and so on.

The $C_1$–$C_6$ carboxamido group is a straight or branched carboxylic acylamino group such as formamido, acetamido, propionamido, butyramido, isobutyramido, valeramido and so on.

The $C_3$–$C_6$ cycloalkyl group is a monocycloalkyl group such as cyclopropyl, cyclobutyl, cyclopentyl, cyclohexyl and so on.

The $C_6$–$C_{10}$ aryl group is a monocyclic or bicyclic aromatic hydrocarbon group such as phenyl and naphtyl.

The $C_7$–$C_{14}$ aralkyl group is an alkyl group of 1 to 4 carbon atoms linked to a monocyclic or bicyclic aromatic hydrocarbon group of 6 to 10 carbon atoms. Examples of aralkyl groups are benzyl, phenylethyl and naphtylmethyl.

The heterocyclyl group is a 5- or 6-membered, saturated or unsaturated heterocyclyl ring, containing at least one heteroatom selected from O, S and N, which is optionally fused to a second 5- or 6-membered, saturated or unsaturated heterocyclyl group as above defined, or to a $C_3$–$C_6$ cycloalkyl group, or to a phenyl group.

The above said alkyl, alkenyl, alkoxy, alkylthio, aryl, aralkyl, heterocyclyl groups can be either unsubstituted or substituted by one or more substituents selected from the following ones:

halo (i.e., fluoro, bromo, chloro or iodo);

hydroxy;

nitro;

azido;

amino (i.e., —$NH_2$, or —NHR' or —NR'R") wherein R' and R", which may be the same or different, are $C_1$–$C_6$ straight or branched alkyl, phenyl or benzyl;

formyl (i.e., —CHO);

mercapto (i.e., —SH or —SR') wherein R' is as defined above;

cyano;

carboxy(alkyl) (i.e., $(CH_2)_t$COOH or $(CH_2)_t$COOR' wherein R' is as defined above and t is 0, 1, 2 or 3;

sulpho (i.e., —$SO_3H$);

acyl (i.e., —C(O)R' wherein R' is as defined above or trifluoroacetyl (i.e., —C(O)$CF_3$);

carbamoyl (i.e., —$CONH_2$); N-methylcarbamoyl (i.e., —$CONHCH_3$) or N-carboxymethylcarbamoyl (i.e., —$CONHCH_2COOH$);

carbamoyloxy (i.e., —$OCONH_2$);

acyloxy (i.e., —OC(O)R') wherein R' is as defined above or formyloxy (i.e., —OC(O)H);

alkoxycarbonyl or benzyloxycarbonyl (i.e., —C(O)OR') wherein R' is as defined above;

alkoxycarbonyloxy or benzyloxycarbonyloxy (i.e., —OC(O)OR') wherein R' is as defined above;

alkoxy, phenoxy or benzyloxy (i.e., —OR') wherein R' is as defined above;

alkylthio, phenylthio or benzylthio (i.e., —SR') wherein R' is as defined above;

alkylsulphinyl, phenylsulphinyl or benzylsulphinyl (i.e., —S(O)R') wherein R' is as defined above;

alkylsulpbonyl, phenylsulphonyl or benzylsulphonyl (i.e., —$S(O)_2R'$) wherein R' is as defined above;

acylamino (i.e., —NHC(O)R''' or —NHC(O/OR''') wherein R''' is $C_1$–$C_6$ straight or branched alkyl, phenyl, benzyl, $CH_2CH_2COOH$ or $CH_2CH_2CH_2COOH$;

sulphonamido (i.e., —$NHSO_2R'$) wherein R' as defined above;

guanidino (i.e., —NHC(=NH)$NH_2$);

$C_1$–$C_4$ alkyl, $C_2$–$C_4$ alkenyl or alkynyl;

phenyl;

$C_3$–$C_6$ cycloalkyl;

substituted methyl selected from chloromethyl, fluoromethyl, difluoromethyl, trifluoromethyl, aminomethyl, dimethylaminomethyl, azidomethyl, cyanomethyl, carboxymethyl, sulphomethyl, carbamoylmethyl, [2-methyl-5-oxo-2,5 dihydro-5-hydroxy-1,2,4 triazin-3-yl] thiomethyl, carbamoyloxymethyl, hydroxymethyl, $C_1$–$C_4$ alkoxy carbonylmethyl, guanidinomethyl, carbamoyloxymethyl.

The hydroxy protecting group may, for example, be a lower alkylsilyl group such as trimethylsilyl, tert-butyldimethylsilyl, tert-butyldiphenylsilyl; a lower alkoxymethyl group such as methoxymethyl or 2-methoxyethoxymethyl, a tetrahydropyranyl group; an aralkyl group such as benzyl, p-methoxybenzyl, 3,4-dimethoxybenzyl, o-nitrobenzyl, p-nitrobenzyl, benzhydryl, bis(p-methoxyphenyl)methyl, trityl; an acyl group such as formyl or acetyl; a lower alkoxycarbonyl group such as tert-butoxycarbonyl, 2,2,2-trichloroethoxycarbonyl, 2-iodoethoxycarbonyl; an alkenyloxycarbonyl group such as 2-propenyloxycarbonyl, 2-chloro-2-propenyloxycarbonyl, 3-methoxycarbonyl-2-propenyloxycarbonyl, 2-methyl-2-propenyloxycarbonyl, 2-butenyloxycarbonyl, cinnamyloxycarbonyl; an aralkyloxycarbonyl group such as benzyloxycarbonyl, p-methoxybenzyloxycarbonyl, o-nitrobenzyloxycarbonyl, p-nitrobenzyloxycarbonyl. Particularly preferred are a 2-propenyloxycarbonyl group, a p-nitrobenzyloxycarbonyl group, a p-methoxybenzyloxycarbonyl group, a tert-butoxycarbonyl group, 2,2,2-trichloroethoxycarbonyl group, a lower alkylsilyl group such as trimethylsilyl or tertbutyldimethylsilyl, tert-butyldiphenylsilyl group.

The amino, hydroxy or mercapto protecting groups possibly present may be those usually employed in the chemistry of penicillins and cephalosporins for this kind of functions. They may be, for instance, optionally substituted, especially halo-substituted, acyl groups, e.g. acetyl, monochloroacetyl, dichloroacetyl, trifluoroacetyl, benzoyl or p-bromophenacyl; triarylmetylgroups, e.g. triphenylmethyl; silyl groups, in particular trimethylsilyl, dimethyl-tert-butylsilyl, diphenyl-tert-butylsilyl, or also groups such as tert-butoxycarbonyl, p-nitrobenzyloxycarbonyl, 2,2,2-trichloroethoxycarbonyl, benzyl and pyranyl.

The carboxyl-protecting group may, for example, be a lower alkyl group such as methyl, ethyl, propyl, isopropyl or tert-butyl; a halogenated lower alkyl group such as a 2,2,2-trichoroethyl or a 2,2,2-trifluoroethyl; a lower alkanoyloxyalkyl group such as acetoxymethyl, propionyloxymethyl, pivaloyloxymethyl, 1-acetoxyetyl, 1-propionyloxyethyl; a lower alkoxycarbonyloxyalkyl group such as 1-(methoxycarbonyloxy)ethyl, 1-(ethoxycarbonyloxy)ethyl, 1-(isopropoxycarbonyloxy)ethyl; a lower alkenyl group such as 2-propenyl, 2-chloro-2-propenyl, 3-methoxycarbonyl-2-propenyl, 2-methyl-2-propenyl, 2-butenyl, cinnamyl; an aralkyl group such as benzyl, p-methoxybenzyl, 3,4-dimethoxybenzyl, o-nitrobenzyl, p-nitrobenzyl, benz-hydryl, bis(p-methoxyphenyl)methyl; a (5-substituted 2-oxo-1,3-dioxol-4-yl)methyl group such as (5-methyl-2-oxo-1,3-dioxol-4-yl)methyl; a lower alkylsilyl group such as trimethylsilyl, tert-butyldimethylsilyl, tert-butyldiphenylsilyl, triphenylsilyl; or an indanyl group; a phtalidyl group; a pyranyl group; a metoxymethyl or methylthiomethyl group; a 2-methoxyethoxymethyl group.

Particularly preferred are a 2-propenyl group, a p-nitrobenzyl group, a p-methoxybenzyl group, a benzhydryl group, a tert-butyl group, a tert-butyldimethylsilyl or tert-butyldiphenylsilyl group.

The present invention provides the salts of those compounds of formula (I) that have salt-forming groups, especially the salts of the compounds having a carboxylic group or a basic group (e.g. an amino or guanidino group). The salts are especially tolerable salts, for example alkali metal and alkaline earth metal salts (e.g. sodium, potassium, lithium, calcium and magnesium salts), ammonium salts and salts with an appropriate organic amine or amino acid (e.g. arginine, procaine salts), and the addition salts formed with suitable organic or inorganic acids, for example hydrochloric acid, sulphuric acid, carboxylic and sulphonic acids (e.g. acetic, trifluoroacetic, p-toluensulphonic acid).

The present invention encompasses all the possible stereoisomers and tautomers, as well as their racemic or optically active mixtures.

Particularly preferred compounds are those represented by formula (I')

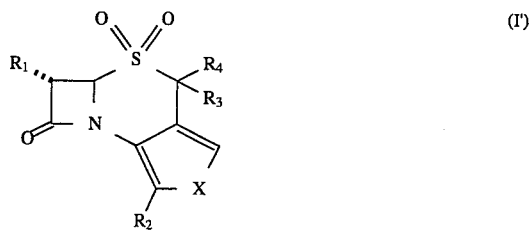

wherein $R_1$ is either hydrogen or a fluorine or chlorine atom; or methyl, ethyl, propyl, iso-propyl, n-butyl, 2-methyl-1-propyl, allyl, methallyl, crotyl, 3-methyl-2-buten-1yl, methoxy, ethoxy, propoxy, iso-propoxy, n-butoxy, methylthio, ethylthio, propylthio, isopropylthio, n-butylthio, formyloxy, acetoxy, propionyloxy, butyryloxy, formamido, acetamido, propionamido;

$R_2$ is hydrogen, or methyl, ethyl, propyl, iso-propyl, butyl, 2-methyl-1-propyl, neo-pentyl, 1,1-dimethylpropyl, vinyl, 1-propenyl, 2-methyl-1-propenyl, benzyl, cyclopropyl, cyclopentyl, cyclohexyl, phenyl, p-tert-butylphenyl, p-carboxyphenyl, p-sulphophenyl;

$R_3$ is either hydrogen or halogen (especially fluoro, chloro or bromo) or methyl, ethyl, methoxycarbonylmethyl, tert-butoxycarbonylmethyl, carboxymethyl, cyanomethyl, acetonyl, methoxymethyl, methoxyethoxy methyl, acetoxy methyl, benzyl, 4-methoxybenzyl, 4-nitrobenzyl or a —$S(O)_n$—Het group wherein n is 0, 1 or 2 and Het is a heterocyclic group selected from the following:

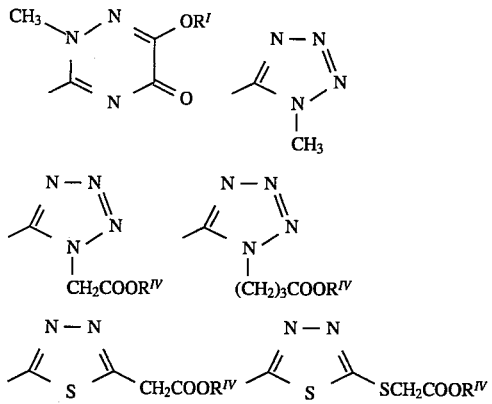

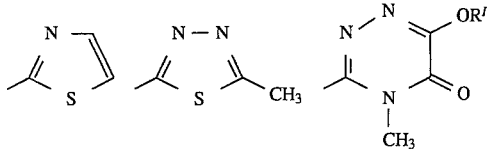
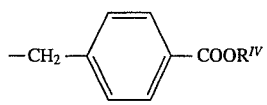

wherein $R^{IV}$ is as defined above;

or $R_4$ taken together with $R_3$ constitutes an ethylene (—$CH_2CH_2$—) or butylene (—$CH_2CH_2CH_2CH_2$—) radical, optionally substituted by one or two methyl or phenyl groups;

and X is as defined for the compounds of the formula I and the pharmaceutical and veterinary acceptable salts thereof, and all the possible stereoisomers and tautomers.

Specific examples of the preferred compounds are listed in Table I.

wherein $R^I$ is hydrogen, methyl, ethyl, allyl, benzyl or a hydroxy protecting group and $R^{IV}$ is hydrogen or methyl, ethyl, allyl, benzyl, or a carboxy protecting group;

$R_4$ is methyl, ethyl, methallyl, crotyl, methoxycarbonylmethyl, tert-butoxycarbonylmethyl, carboxymethyl, cyanomethyl, acetonyl, methoxymethyl, methoxyethoxymethyl, acetoxymethyl, benzyl, 4-methoxybenzyl, 4-nitrobenzyl, benzhydryl, or a group

TABLE 1

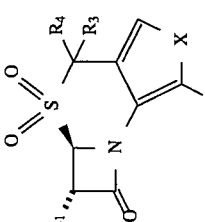

| No. | R$_1$ | R$_2$ | X | R$_3$ | R$_4$ |
|---|---|---|---|---|---|
| 1 | Cl | Bu$^t$ | O | H | H |
| 2 | " | " | " | " | CH$_2$CO$_2$Bu$^t$ |
| 3 | " | φBu$^t$ | " | " | CH$_2$CO$_2$H |
| 4 | " | " | " | " | (α) CH$_3$ |
| 5 | " | " | " | " | (β) CH$_3$ |
| 6 | " | " | " | " | S—TET |
| 7 | " | " | " | " | S—TRI |
| 8 | " | " | " | " | CH$_2$CO$_2$H |
| 9 | " | " | " | " | CH$_2$φ |
| 10 | CH$_3$O | φBu$^t$ | " | " | H |
| 11 | " | Bu$^t$ | " | " | H |
| 12 | " | " | " | " | (α) CH$_3$ |
| 13 | " | " | " | " | (β) CH$_3$ |
| 14 | " | " | " | " | CH$_2$CO$_2$Bu$^t$ |
| 15 | " | " | " | " | CH$_2$CO$_2$H |
| 16 | " | " | " | " | CH$_2$φ |
| 17 | " | " | " | " | CH$_2$φp—CO$_2$Bu$^t$ |
| 18 | CH$_3$O | Bu$^t$ | O | H | CH$_2$φp—CO$_2$H |
| 19 | H | φBu$^t$ | " | " | H |
| 20 | " | φ | " | " | " |
| 21 | " | Bu$^t$ | " | " | " |
| 22 | CH$_2$=CHCH$_2$ | " | " | " | " |
| 23 | CH$_3$CH$_2$CH$_2$ | " | " | " | " |
| 24 | CH$_3$CH$_2$ | Bu$^t$ | " | " | " |
| 25 | CH$_3$O | φBu$^t$ | " | " | " |
| 26 | " | " | " | CH$_3$ | —CH$_2$CH$_2$— |
| 27 | " | " | " | CH$_3$ | —CH$_2$CH(φ)— |
| 28 | " | " | O | CH$_2$φ | —CH$_2$—C(φ)$_2$— |
| 29 | CH$_3$ | Bu$^t$ | O | CH$_2$φp—CO$_2$H | " |
| 30 | " | " | " | " | " |
| 31 | CH$_3$O | Bu$^t$ | O | " | S—TET |
| 32 | " | " | " | " | S—TRI |
| 33 | " | " | " | " | S—TET |
| 34 | " | " | " | " | S—TET |
| 35 | " | " | " | " | Br |
| 36 | " | " | " | " | Cl |
| 37 | " | " | " | " | F |
| 38 | " | " | " | " | —CH$_2$SCH$_2$CO$_2$H |

TABLE 1-continued

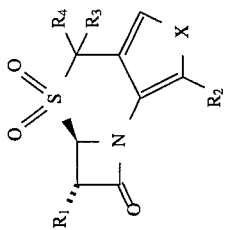

| No. | R₁ | R₂ | X | R₃ | R₄ |
|---|---|---|---|---|---|
| 39 | Cl | φ | S | H | H |
| 40 | CH₃O | Buᵗ | " | " | " |
| 41 | " | φ | " | " | " |
| 42 | " | Buᵗ | " | " | CH₃ |
| 43 | " | " | " | " | CH₂CO₂Buᵗ |
| 44 | " | " | " | " | CH₂CO₂H |
| 45 | " | " | " | " | CH₂φ |
| 46 | " | " | " | " | CH₂φp—CO₂Buᵗ |
| 47 | " | " | " | " | CH₂φp—CO₂H |
| 48 | " | " | " | " | —CH₂CH₂— |
| 49 | " | Buᵗ | " | " | —CH₂—C(φ)₂— |
| 50 | " | " | " | " | S—TET |
| 51 | CH₃O | Buᵗ | S | CH₃ | " |
| 52 | CH₃O | Buᵗ | S | CH₂φ | " |
| 53 | " | " | " | CH₂φp—CO₂H | " |
| 54 | Cl | φ | " | H | H |
| 55 | CH₃O | Buᵗ | NH | " | " |
| 56 | " | " | " | " | CH₃ |
| 57 | " | " | " | " | CHCO₂Buᵗ |
| 58 | " | " | " | " | CH₂CO₂H |
| 59 | " | " | " | " | CH₂φ |
| 60 | " | " | " | " | —CH₂CH₂— |
| 61 | " | " | " | " | —CH₂C(φ)₂— |
| 62 | " | " | " | " | CH₂φp—CO₂Buᵗ |
| 63 | " | " | " | H | CH₂φp—CO₂H |
| 64 | " | " | " | CH₃ | S—TET |
| 65 | " | " | " | CH₂φp—CO₂H | " |
| 66 | " | " | " | H | CH₂CO₂Buᵗ |
| 67 | Cl | " | " | H | CH₂CO₂H |
| 68 | " | " | " | " | CH₂CO₂H |
| 69 | CH₃O | φ—φ | NH | " | " |
| 70 | " | " | " | " | " |
| 71 | CH₃O | " | " | " | CH₃ |
| 72 | Cl | " | " | " | " |
| 73 | CH₃O | " | " | " | CH₂φ |
| 74 | Cl | " | " | " | " |
| 75 | " | " | " | " | —CH₂CH₂— |
| 76 | " | " | " | " | " |
| 77 | CH₃O | " | " | " | " |

TABLE 1-continued

| No. | R₁ | R₂ | X | R₃ | R₄ |
|---|---|---|---|---|---|
| 78 | " | " | " | H | CH₂φp—CO₂H |
| 79 | " | " | " | " | CH₂CO₂H |
| 80 | " | " | " | " | —CH₂C(φ)₂ |
| 81 | " | " | " | " | —CH₂CO₂Buᵗ |
| 82 | OCH₃ | biphenyl | O | H | H |
| 83 | " | Buᵗ | " | " | -S-C(CH₃)=N-N (thiadiazole with CH₃) |
| 84 | " | Ph | " | " | " |
| 85 | " | " | " | " | " |
| 86 | " | " | NH | " | -S-C=N-N-N(CH₃) (tetrazole with CH₃) |
| 87 | " | " | O | " | CH₃N=C(OH)—C(=O)—O—S- |
| 88 | " | " | " | " | " |
| 89 | " | " | NH | " | -S-C=N-N (thiadiazole with SCH₂CO₂H) |
| 90 | " | " | " | " | " |

TABLE 1-continued
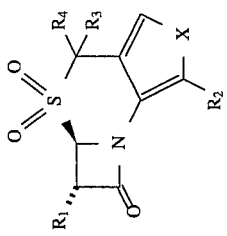
| No. | R₁ | R₂ | X | R₃ | R₄ |
|---|---|---|---|---|---|
| 91 | " | " | O | " | " |
| 92 | " | " | S | " | " |
| 93 | " | " | " | " | $-S-C(=N-N=N)-N(CH_2CO_2H)$ |
| 94 | " | " | O | " | " |
| 95 | OCH₃ | Ph | NH | " | " |
| 96 | " | Buᵗ | N—CH₂COOH | H | H |
| 97 | " | " | N—CH₂C(O)C(CH₃)₃ | " | " |
| 98 | " | Ph | " | " | " |
| 99 | " | " | " | " | " |
| 100 | " | " | N—CH₂—C₆H₄—NO₂ | " | " |
| 101 | " | Buᵗ | " | " | " |
| 102 | " | " | " | " | " |
| 103 | " | Ph | N—CH₂—C₆H₄—CO₂H | " | " |
| 104 | " | " | " | " | " |
| 105 | " | Buᵗ | " | " | $-S-C(=N-N=N)-NHCH_3$ |

TABLE 1-continued

| No. | R₁ | R₂ | X | R₃ | R₄ |
|---|---|---|---|---|---|
| 106 | " |  | " | " | $-S-\underset{\|}{C}=N-N=\underset{\|}{C}-CH_3$ (thiadiazole with CH₃) |
| 107 | " | Ph | " | " | " |
| 108 | " | " | N—CH₂CO₂CH₂CH=CH₂ | " | " |
| 109 | " | Buᵗ | N—CH₂CO₂C(CH₃)₃ | " | " |
| 110 | " | Ph | " | " | " |
| 111 | " | " | " | " | $CH_3-\underset{\|}{N}-N=\underset{\|}{C(OH)}-C(=O)-N=\underset{\|}{C}-S-$ |
| 112 | " | " | " | " | " |
| 113 | " | Buᵗ | N—CH₂COOH | " | " |
| 114 | " | " | " | " | " |
| 115 | " | Ph | " | " | $CH_3-\underset{\|}{N}-N=\underset{\|}{C(OH)}-C(=O)-N=\underset{\|}{C}-S-$ |
| 116 | OCH₃ | Ph | N—CH₂—C₆H₄—CO₂H | H | H |
| 117 | " | Buᵗ | N—CH₂—C₆H₄—CO₂C(CH₃)₃ | " | " |
| 118 | " | " | " | " | " |
| 119 | " | Ph | " | " | " |

Core structure: β-lactam with sulfone (SO₂), substituents R₁ (α to sulfone), R₂ on adjacent carbon, X in ring, R₃ and R₄ on CH group.

TABLE 1-continued
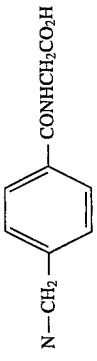
| No. | R₁ | R₂ | X | R₃ | R₄ |
|---|---|---|---|---|---|
| 120 | " | " | 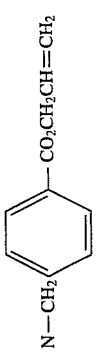 N—CH₂—C₆H₄—CONHCH₂CO₂H | " | " |
| 121 | " | Buᵗ | " | " | " |
| 122 | " | " | N—CH₂—C₆H₄—CO₂CH₂CH=CH₂ | " | " |
| 123 | " | Ph | " | " | " |
| 124 | " | " | " | " | " |
| 125 | " | Buᵗ | " | " | —S—C(=N-N=N)NHCH₃ |
| 126 | " | " | N—CH₂—C₆H₄—CO₂C(CH₃)₃ | " | " |
| 127 | " | Ph | " | " | " |
| 128 | " | " | " | " | H |
| 129 | " | Buᵗ | " | " | " |
| 130 | " | " | " | " | 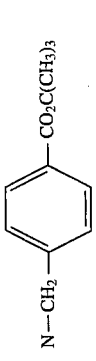 |
| 131 | " | Ph | " | " | " |

TABLE 1-continued
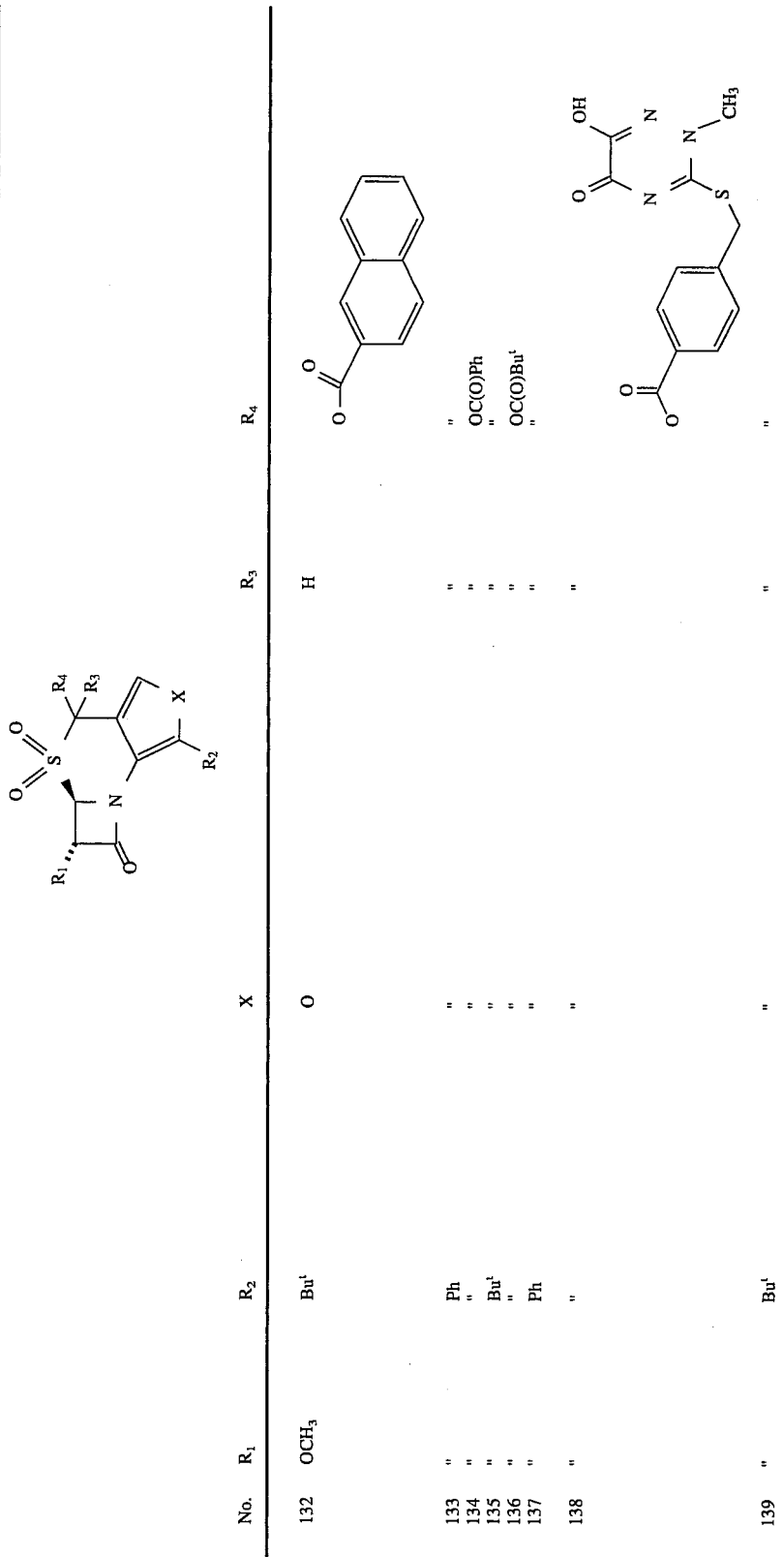
| No. | R₁ | R₂ | X | R₃ | R₄ |
|---|---|---|---|---|---|
| 132 | OCH₃ | Buᵗ | O | H | (2-naphthoate) |
| 133 | " | Ph | " | " | " |
| 134 | " | " | " | " | OC(O)Ph |
| 135 | " | Buᵗ | " | " | OC(O)Buᵗ |
| 136 | " | " | " | " | " |
| 137 | " | Ph | " | " | " |
| 138 | " | " | " | " | (benzoate with S-TRI substituent) |
| 139 | " | Buᵗ | " | | |
φ = phenyl group; Buᵗ = tert-butyl group;
S—TRI = 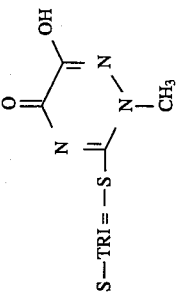

TABLE 1-continued

| No. | R₁ | R₂ | X | R₃ | R₄ |
|-----|----|----|----|----|----|
| S—TET= —S—⟨tetrazole N=N, N—CH₃⟩ | | | | | |

The present invention relates also to the preparation of cephalosporin sulphones of formula (I). Accordingly, the compounds of the present invention can be prepared by a process which comprises:

(i) cyclizing a compound of the formula (II)

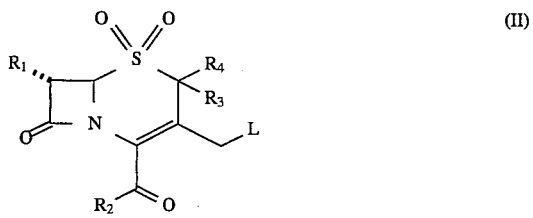

where $R_1$, $R_2$, $R_3$, $R_4$ are as above described, and L is either a group XH, wherein X is as described above, or a leaving group selected from the group consisting of: halogen atoms, in particular Br and I; $C_1$–$C_4$ acyloxy, in particular formyloxy and acetoxy; alkane- or arene-sulphonyloxy, in particular mesyl oxy $CH_3SO_2O$—, p-toluenesulphonyloxy $CH_3$—$C_6H_4$—$SO_2O$—;

(ii) if desired, converting the resulting compound of formula (I) into a pharmaceutical or veterinarily acceptable salt thereof in the step (i) above. When L is a group XH the corresponding compounds of formula (I) are obtained, whereas when L is a leaving group as described above, compounds of formula (I) wherein X is oxygen are obtained.

The cyclization of compounds of formula (II) to give compounds of formula (I) may take place either in aqueous or in organic solvents, or in a mixture of water and a water-soluble solvent, at temperatures ranging from –20° C. to about 110° C., preferably between ca. –5° C. and ca. +40° C., optionally in the presence of an acid or base catalyst. Acid catalysts include mineral acids, such as HCl, $H_2SO_4$ and $H_3PO_4$; carboxylic acid, such as formic acid, acetic acid and trifluoroacetic acid; and sulphonic acids, such as methane-sulphonic acid, trifluoromethanesulphonic acid and p-toluene-sulphonic acid. Base catalysts include inorganic bases, such as NaOH, KOH, and organic bases, such as triethylamine (TEA), pyridine, 4-dimethylaminopyridine, 1,5-diazabicyclo[4.3.0]non-5-ene (DBN), 1,4-diazabicyclo[2.2.2]octane (DBO), 1,8-diazabicyclo[5.4.0]undec-7-ene (DBU).

The intermediates of formula (II) are known, or may be prepared from known compounds according to methologies known per-se. For example, intermediates of formula (II) wherein L is OH, $OCOCH_3$, Br are known (see EP-A-0337704). Intermediates of formula (II) wherein L is SH can be prepared, for example, from the corresponding compound wherein L is Br. Preferred procedures illustrated in the preparations, include reaction with thiolacetic acid ($CH_3COSH$) followed by methanolys or is followed by sequential treatment with silver trifluoromethanesulphonate and aqueous HCl. Intermediates of formula (II) wherein L is $NR_6$ can be prepared from the corresponding compounds wherein L is Br by reaction with the corresponding amine $HNR_6$, or with an azide salt, e.g. $AgN_3$, followed by reduction to the compound of formula (II) wherein L is $NH_2$ e.g. by treatment with triphenylphosphine. In many cases, intermediates of formula (II) wherein L is XH need not to be isolated, since condensation to the corresponding compounds of formula (I) usually occur under very mild conditions and may be spontaneous.

It is understood that in the process above any functional group, if needed or desired, can be masked by conventional methods and unmasked at the end or when convenient. It is also understood that the groups $R_1$, $R_2$, $R_3$, $R_4$ and $R_5R_6$ can be converted by conventional methods into different groups included within those previously defined, if desired, at the end or at any stage of the process above. This conversion or masking/unmasking of the protecting groups are well known in cephalosporin area (see, e.g. "Cephalosporins and Penicillins", E. H. Flynn Ed.).

The potentialities of protease inhibitor therapy in the treatment of conditions resulting from the destruction of connective tissues have recently received particular attention. Much effort has been devoted to the search for inhibitors of human leukocyte elastase (HLE), which is the primary destructive agent in pulmonary emphysema and is probably involved in rheumatoid arthritis (J. C. Power, Am. Rev. Resp. Diseases 127, S54-S58, 1983; C. H. Hassal et al, FEBS Letters, 183, n. 2, 201, 1985, G. Weinbaum and V. V. Damiano, TIPS, 8, 6, 1987; M. Velvart, Rheumatol. Int. 1, 121, 1981). Low molecular weight inhibitors appear to have a number of advantages over natural high molecular weight protease inhibitors from either plant or animal sources: 1) they can be obtained in quantities; 2) they can be rationally designed or optimised; 3) they are not antigenic; and 4) they may be used orally or in aerosols. Many low molecular weight elastase inhibitors discovered so far contain reactive functional groups (chloromethyl ketones, isocyanates, etc); they may react with functional groups of proteins, and therefore they may be quite toxic. In this respect, β-lactam compounds are of potential interest because, though reactive towards serine proteases, they are, as it is known, non-toxic at very high concentrations.

The compounds of the present invention are characterized by high inhibitory activity on elastases, especially human leukocyte elastase (HLE).

Owing to their high elastase-inhibiting activity and their quite negligible toxicity, the compounds of the present invention can be used in the treatment of inflammatory and degenerative diseases caused by proteolytic enzymes in mammals including humans. The compounds can be used to make medicaments useful to prevent or arrest the progression of diseases caused by proteolytic degradation of lungs and connective tissues, reduce inflammation and fever, and relieve pain. Such diseases are emphysema, cystic fibrosis, acute respiratory distress syndrome, bronchial inflammation, rheumatoid arthritis, osteoarthritis, infectious arthritis, rheumatic fever, spondylitis, gout, lupus, psoriasis, and the like. Moreover, they may be usefully employed in the control of tumor invasion Accordingly, the present invention also provides pharmaceutical and veterinary compositions containing a suitable carrier and/or diluent and, as an active principle, a 4-acylcephem sulphone of formula I or a pharmaceutically or veterinarily acceptable salt thereof. The pharmaceutical or veterinary compositions containing a compound of formula I or salt thereof may be prepared in a conventional way by employing conventional non-toxic pharmaceutical carriers or diluents in a variety of dosage forms and ways of administration. In particular, the compounds of formula I can be administered:

A)

Orally, for example, as tablets, troches, lozenges, aqueous or oily suspensions, dispersible powders or granules, emulsions, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the active ingredient in admixture with non-toxic pharmaceutically acceptable excipients which are suitable for the manufacture of tablets.

These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc.

The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed.

Formulation for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions contain the active materials in admixture with excipients suitable for the manufacture of aqueous suspensions.

Such excipients are suspending agents, for example, sodium carboxymethylcellulose, methylcellulose, hydroxypropylmethylcellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl or n-propyl p-hydroxybenzoate, one or more coloring agents, one or more flavoring agents, or one or more sweetening agents, such as sucrose or saccharin. Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives.

Suitable dispersing or wetting agents and suspending agents are exemplified by those already mentioned above.

Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsion may also contain sweetening and flavoring agents.

Syrups and elixirs may be formulated with sweetening agents, for example glycerol, sorbitol or sucrose.

Such formulations may also contain a demulcent, a preservative and flavoring and coloring agents.

B)
Parenterally, either subcutaneously, or intravenously, or intramuscularly, or intrasternally, or by infusion techniques, in the form of sterile injectable aqueous or olagenous suspensions. The pharmaceutical compositions may be in the form of a sterile injectable aqueous or olagenous suspension.

This suspension may be formulated according to the known art using those suitable dispersing of wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium.

For this purpose any bland fixed oil may be employed including synthetic mono- or diglycerides. In addition fatty acids such as oleic acid find use in the preparation of injectables;

C)
By inhalation, in the form of aerosols or solutions for nebulizers;

D)
Rectally, in the form of suppositories prepared by mixing the drug with a suitable non-irratating excipient which is solid at ordinary temperature but liquid at the rectal temperature and will therefore melt in the rectum to release the drug. Such materials are cocoa butter and poly-ethylene glycols;

E)
Topically, in the form of creams ointments, jellies, solutions or suspensions.

Still a further object of the present invention is to provide a method of controlling inflammatory and degenerative diseases by administering a therapeutically effective amount of one or more of the active compounds encompassed by the formula I in humans or mammalians in need of such treatment. Daily dose are in the range of about 0.1 to about 50 mg per kg of body weight, according to the activity of the specific compound, the age, weight and conditions of the subject to be treated, the type and severity of the disease, and the frequency and route of administration; preferably, daily dosage levels for humans are in the range of 20 mg to 2 g. The amount of active ingredient that may be combined with the carrier materials to produce a single dosage form will vary depending upon the host treated and the particular mode of administration. For example, a formulation intended for the oral administration to humans, may contain from 5 mg to 2 g of active agent compounded with an appropriate and convenient amount of carrier material which may vary from about 5 to about 95 percent of the total composition. Dosage unit forms will generally contain between from about 5 mg to about 500 mg of active ingredient.

EXPERIMENTAL PART

EXAMPLE 1

4'-tert-Butyl-(7α)-chlorofuro[3,4-c]cepham 1,1-dioxide (Compound 1)

A mixture of 3-acetoxymethyl-4-tert-butylcarbonyl-(7α)-chloro-3-cephem 1,1-dioxide (54 mg) in dioxane (2 ml) and 2N hydrochloric acid (1 ml) was stirred at room temperature for 6 hours, then poured into ethyl acetate/water. The organic phase was washed twice with brine, then aq. $NaHCO_3$. After drying over $Na_2SO_4$, the solvent was removed under reduced pressure. The crude material was chromatographed on silica gel eluting with cyclohexane/EtOAc mixtures. The title product was obtained as a white solid (34 mg).

IR (KBr) 1786 $cm^{-1}$.

NMR ($CDCl_3$, 200 MHz): δ1.37 (9H,s); 4.28 (2H,d,J=1.3 Hz); 4.81 (1H,d,J=1.4 Hz); 5.30 (1H,d,J=1.4 Hz); 7.15 (1H,t,J=1.3 Hz).

EXAMPLE 2

(7α)-Methoxy-4'-phenylfuro[3,4-c]cepham 1,1-dioxide (Compound 11)

A solution of 3-bromomethyl-(7α)-methoxy-4-phenylcarbonyl-3-cephem 1,1-dioxide (90 mg) in ethyl acetate (5 ml) was treated with triethylamine (50 ml). After standing for i hour at room temperature, the reaction mixture was diluted with ethyl acetate and washed with 1N hydrochloric acid, then brine. After drying over $Na_2SO_4$, the solvent was removed in vacuo and the residue was chromatographed ($SiO_2$; EtOAc/cyclohexane mixtures as eluants). The title product was obtained as a white powder.

IR (KBr) 1784 $cm^{-1}$.

NMR ($CDCl_3$, 200 MHz): δ3.62 (3H,s); 4.31 (2H,d,J=1.3 Hz); 4.83 (1H,d,J=1.4 Hz); 5.20 (1H,d,J=1.4 Hz); 7.31 (1H,d,J=1.3 Hz); 7.3–7.8 (5H,m). UV (EtOH) $\lambda_{max}$ 286 nm.

EXAMPLE 3

4'-tert-Butyl-(7α)-methoxyfuro[3,4-c]cepham 1,1-dioxide (Compound 12)

To a stirred solution of 3-bromomethyl-4-tert-butylcarbonyl-3-cephem 1,1-dioxide (1.85 g) in dichloromethane (100 ml) N,N-diisopropyl-N-ethylamine (0.86) was added dropwise. The resulting solution was stirred at room temperature for 2 hours (monitoring by IR spectroscopy the disappearance of the ketonic band at 1700 $cm^{-1}$). Following washing with 2% aqueous HCl, the organic phase was rinsed with brine then dried ($Na_2SO_4$) and rotoevaporated. The residue was purified by flash chromatography affording the title product as a white solid (1 g).

IR (KBr) 1790 $cm^{-1}$

NMR ($CDCl_3$, 200 MHz): δ1.37 (9H,s); 3.57 (3H,s); 4.23 (2H,d,J=1.3 Hz); 4.71 (1H,d,J=1.2 Hz); 5.16 (1H,d,J=1.2 Hz); 7.13 (1H,t,J=1.3 Hz).

EXAMPLE 4

4'-tert-Butyl-(7α)-methoxy-(2α)-methylfuro [3,4-c]cepham 1,1-dioxide (Compound 13)

A solution of 4-tert-butylcarbonyl-3-hydroxymethyl-(7α)-methoxy-(2α)-methyl-3-cephem 1,1-dioxide (15 mg) in acetone (2 ml) and water (1 ml) was treated with para-toluensulphonic acid monohydrate (15 mg). After stirring for 3.5 hours at room temperature the reaction mixture was poured into EtOAc/water. The organic phase was dried ($Na_2SO_4$) and concentrated. Following purification by flash chromatography the title product was obtained as a white solid (10 mg).

IR (KBr) 1782 $cm^{-1}$.

EXAMPLE 5

4'tert-Butyl-(7α)-methoxy-(2β)-methylfuro [3,4-c]cepham 1,1-dioxide (Compound 14)

A solution of 3-bromomethyl-4-tert-butylcarbonyl-(7α)-methoxy-(2β)-methyl-3-cephem 1,1-dioxide (40 mg) in acetone (3 ml) and water (1 ml) was treated with silver triflate (30 mg) and stirred for 30 minutes at room temperature. The mixture was then poured into ethyl acetate-4% aqueous $NaHCO_3$. The upper phase was separated, dried ($Na_2SO_4$) and evaporated. The residue was chromatographed over silica gel (eluting with cyclohexane/EtOAc mixtures) to afford the title product as a white solid (20 mg).

IR (KBr) 1795 $cm^{-1}$.

NMR ($CDCl_3$, 200 MHz): δ1.37 (9H,s); 3.60 (3H,s); 4.27 (1H,dq,J=1.7 and 6.7 Hz); 4.74 (1H,br-s); 5.19 (1H,d,J=1.1 Hz); 7.08 (1H,d,J=1.7 Hz).

EXAMPLE 6

(2α)-tert-Butoxycarbonylmethyl-4'-tert-butyl-(7α)-methoxyfuro[3,4-c]cepham 1,1-dioxide (Compound 15)

A solution of 3-bromomethyl-(2α)-tert-butoxycarbonylmethyl-4'-tert-butyl-(7α)-methoxy-3-cephem 1,1-dioxide (180 mg) in acetonitrile (10 ml) was treated with N,N-diisopropyl-N-ethylamine (86 μl) and let stand at room temperature for 30 minutes.

An additional amount of Hunig base (86 μg) was added and the mixture was let stand for 6 hours. After pouring into EtOAc-2% aqueous HCl the organic phase was dried ($Na_2SO_4$) and concentrated. The resulting syrup was chromatographed over silica gel (eluting with EtOAc/cyclohexane mixtures) and the title product was obtained as a white solid (110 mg).

IR (KBr) 1795, 1730 $cm^{-1}$.

NMR ($CDCl_3$, 200 MHz): δ1.36 (9H,s); 1.43 (9H,s); 2.81 (1H,dd,J=8.9 and 16.5 Hz); 3.13 (1H,dd,J=4.4 and 16.5 Hz); 3.57 (3H,s); 4.56 (1H,ddd,J=0.9, 4.4 and 8.9 Hz); 4.75 (1H,d,J=1.3 Hz); 5.18 (1H,d,J=1.3 Hz); 7.15 (1H,d,J=0.9 Hz).

EXAMPLE 7

4α-tert-Butyl-(2α)-carboxymethyl-(7α)-methoxyfuro[3,4-c]cepham 1,1-dioxide (Compound 16)

A solution of (2α)-tert-butoxycarbonylmethyl-4'-tert-butyl-(7α)-methoxyfuro[2,3-c]cepham 1,1-dioxide (75 mg) in dichloromethane (3 ml) was sequentially treated with anisole (200 μl) and trifluoroacetic acid (2 ml) and let stand at room temperature for 90 minutes.

Removal of the solvent and treatment of the residue with diisopropyl ether-petrol ether allowed the isolation of the title product as a white solid (60 mg).

IR (KBr) 3600–2500, 1790, 1715 cm$^{-1}$.

NMR (CDCl$_3$, 200 MHz): δ1.36 (9 h,s); 2.96 (1H,dd,J= 9.0 and 17.2 Hz); 3.30 (1H,dd,J=4.3 and 17.2 Hz); 3.57 (3H,s); 4.60 (1H,ddd,J=0.9, 4.3 and 9.0 Hz); 4.74 (1H,d,J= 1.3 Hz); 5.19 (1H,d,J=1.3 Hz), 7.17 (1H,d,J=0.9 Hz).

Method B

3-Acetylthiomethyl-4-tert-butylcarbonyl-(7α)-methoxy-3-cephem 1,1-dioxide (20 mg) was dissolved in methyl alcohol (2 ml) and treated with silver triflate (50 mg). After stirring for 30 hours at room temperature, acetone (1 ml) and 1N hydrochloric acid (1.5 ml) were added. The resulting mixture was stirred for 30 minutes then poured into EtOAc/water and processed as indicated in Method A to afford the title product as a white powder (12 mg).

To afford the title product as a white powder (12 mg).

EXAMPLE 8

4'-tert-Butyl-(7α)-methoxythieno[3,4-c]cepham 1,1-dioxide (Compound 42)

Method A

A solution of 3-acetylthiomethyl-4-tert-butylcarbonyl-(7α)-methoxy-3-cephem 1,1-dioxide (25 mg) was dissolved in methyl alcohol (2.5 ml) was treated with 37% hydrochloric acid (0.3 ml). After standing for 18 hours at room temperature the reaction mixture was poured into EtOAc/water. The organic phase was dried (Na$_2$SO$_4$) and concentrated. Following flash chromatography over silica gel (cyclohexane/ethyl acetate mixtures as eluants) the title product was obtained as a white solid (14 mg).

IR (KBr) 1782 cm$^{-1}$.

NMR (CDCl$_3$, 200 MHz): δ1.46 (9H,s); 3.59 (3H,s); 4.07 (1H,dd,J=1.4 and 15.4 Hz); 4.28 (1H,dd,J=1.2 and 15.4 Hz); 4.58 (1H,t,J=~1.4 Hz); 5.14 (1H,d,J=1.5 Hz); 7.01 (1H,d,J= 1.2 Hz). FD-MS: 315 (M$^+$).

EXAMPLE 9

4'-tert-Butyl-(7α)-methoxypyrrolo[3,4-c]cepham 1,1-dioxide (Compound 55)

Triphenylphosphine (45 mg) was added to a solution of 3-azidomethyl-4-tert-butylcarbonyl-(7α)-methoxy-3-cephem 1,1-dioxide (50 mg) in dichloromethane (8 ml). After stirring for 4 hours at room temperature the solvent was removed in vacuo and the residue was chromatographed over silica gel (eluting with cyclohexane-ethyl acetate mixtures). The title product was obtained as a white foam (32 mg).

IR (CHCl$_3$) 3480, 1785 cm$^{-1}$.

NMR (CDCl$_3$, 200 MHz): δ1.39 (9H,s); 3.57 (3H,s); 4.17 (1H,d,J=15.7 Hz); 4.31 (1H,d,J=15.7 Hz); 4.65 (1H, br-s); 5.14 (1H,d,J=1.2 Hz); 6.44 (1H,d,J=3.0 Hz; 8.03 (1H, broad).

EXAMPLE 10

7α-Methoxy-4'-(4-phenyl)phenyl-furo[3,4-c]cepham1,1-dioxide (compound 82)

Starting from 3-bromomethyl-7α-methoxy-4-(4-phenyl)phenylcarbonyl-3-cephem 1,1-dioxide and following the procedure described in Example 3 the title product was obtained as a white powder.

IR (KBr) ν$_{max}$ 1775 cm$^{-1}$

NMR (CDCl$_3$, 200 MHz) δ3.65 (3H, s); 4.34 (2H, s); 4.86 (1H, d, J=1 Hz); 5.24 (1H, d, J=1.0 Hz); 7.2–7.8 (10H, m).

EXAMPLE 11

4'-tert-Butyl-7α-methoxy-2-(1-methyl-1,2,3,4-tetrazol-5-yl)thio-furo[3,4-c]cepham 1,1-dioxide (compound 7)

A solution of 3-acetoxymethyl-4-tert-butylcarbonyl-7α-methoxy-2-(1-methyl-1,2,3,4-tetrazol-5-yl)thio-3-cephem1,1dioxide (105 mg) in 1:1 dioxane/1N hydrochloric acid (10 ml) was heated at 60 ° C. for 2 hours, then chilled to room temperature and poured into EtOAc/water. After washing with aqueous NaHCO$_3$, the organic phase was dried (Na$_2$SO$_4$) and rotoevaporated under reduced pressure. The residue was treated with dichloromethane/diisopropyl ether/n-hexane, affording the title product as a white powder (80 mg) (obtained as a 6:4 epimeric mixture).

IR (KBr) ν$_{max}$ 1790 cm$^{-1}$

NMR (CDCl$_3$, 200 MHz): the epimeric C-2 protons appear as multiplets at 6.01 δand 6.09 δ.

EXAMPLE 12

Following a procedure similar to that described in Example 11 the following products were obtained:

4'-tert-Butyl-7α-methoxy-2-pivaloyloxy-furo [3,4-c]cepham 1,1-dioxide (compound 135)

IR (KBr) ν$_{max}$ 1780, 1755 cm$^{-1}$

NMR (CDCl$_3$, 200 MHz) δ1.25 (9H, s); 1.41 (9H, s); 3.60 (3H, s); 4.83 (1H, d, J=1.1 Hz); 5.19 (1H, d, J=1.1 Hz); 6.49 (1H, s); 7.35 (1H, s).

4'-tert-Butyl-7α-methoxy-2-(β-naphthoyloxy)-furo[3,4-c]cepham 1,1-dioxide (compound 132)

IR (KBr) ν$_{max}$ 1795, 1735 cm$^{-1}$

NMR (CDCl$_3$, 200 MHz) δ1.42 (9H, s); 3.64 (3H, s); 5.18 (1H, d, J=1.3 Hz); 5.26 (1H, d, J=1.3 Hz); 6.79 (1H, s); 7.50 (1H, s); 7.6–8.8 (7H, m).

4'-tert-Butyl-7α-methoxy-2-(5-methyl-1,3,4-thiadiazol-2-yl)thio-furo[3,4-c]cepham 1,1-dioxide (obtained as a 1:1 epimeric mixture) (compound 83)

IR (KBr) ν$_{max}$ 1790 cm$^{-1}$

NMR (CDCl$_3$, 200 MHz): the epimeric C-2 protons appear as multiplets at 6.13 δ and 6.45 δ.

7α-Methoxy-2-(1-methyl-1,2,3,4-tetrazol-5-yl)thio-4'-phenylfuro[3,4-c]cepham 1,1-dioxide (obtained as a 6:4 epimeric mixture) (compound 85)

IR (KBr) ν$_{max}$ 1790 cm$^{-1}$

NMR (CDCl$_3$, 200 MHz): the epimeric C-2 protons appear as multiplets at 6.12 δ and 6.18 δ.

7α-Methoxy-4'-phenyl-2-pivaloyloxy-furo[3,4-c]cepham 1,1-dioxide (compound 137)

IR (KBr) ν$_{max}$ 1790, 1760 cm$^{-1}$

NMR (CDCl$_3$, 200 MHz) δ1.27 (9H, s); 3.65 (3H, s); 4.94 (1H, d, J=1.4 Hz); 5.24 (1H, d, J=1.4 Hz); 6.55 (1H, s); 7.57 (1H, s); 7.3–7.7 (5H, m).

EXAMPLE 13

4'-tert-Butyl-7α-methoxy-2-(2-methyl-5-oxo-2,5-dihydro-5-hydroxy-1,2,4-triazin-3-yl)thio-furo [3,4-c]cepham 1,1-dioxide (compound 8)

A solution of 3-acetoxymethyl-4-tert-butylcarbonyl-2-(5-benzhydryloxy-2-methyl-5-oxo-2,5-dihydro-1,2,4-triazin-3-yl)thio-7α-methoxy-3-cephem 1,1-dioxide (360 mg) in 1:1 dioxane/1N hydrochloric acid (20 ml) was stirred at 40° C. for 4 hours. EtOAc was added to the reaction mixture, the organic phase was separated thence extracted with aqueous sodium bicarbonate. The aqueous layer was acidified with hydrochloric acid and extracted with EtOAc. Upon drying (Na$_2$SO$_4$) and removal of the solvent, the residue was treated with isopropyl ether, affording the title product as a yellowish powder (90 mg) (6:4 epimeric mixture).

IR (KBr) ν$_{max}$ 1795, 1670 cm$^{-1}$

NMR (CDCl$_3$, 200 MHZ) the epimeric C-2 protons appear as multiplets at 6.62 δ and 6.89 δ.

EXAMPLE 14

7α-Methoxy-2-(2-methyl-5-oxo-2,5-dihydro-5-hydroxy-1,2,4-triazin-3-yl)thio-4'-phenyl-furo [3,4-c]cepham 1,1-dioxide (compound 86)

Starting from 3-acetoxymethyl-2-(5-benzhydryloxy-2-methyl-5-oxo-2,5-dihydro-1,2,4-triazin-3-yl)thio-7α-methoxy-4-phenylcarbonyl-3-cephem 1,1-dioxide and following the procedure described in Example 13 the title product was obtained as a white powder (6:4 epimeric mixture).

IR (KBr) ν$_{max}$ 1790, 1660 cm$^{-1}$

NMR (CDCl$_3$, 200 MHz) the epimeric C-2 protons appear as multiplets at 6.71 δ and 7.01 δ.

EXAMPLE 15

7α-Methoxy-4'-phenyl-pyrrolo[3,4-c]cepham 1,1-dioxide (compound 57)

Starting from 3-azidomethyl-7α-methoxy-4-phenylcarbonyl-3-cephem 1,1-dioxide and following the procedure described in Example 9 the title product was obtained as a white powder.

IR (KBr) ν$_{max}$ 3355, 1775 cm$^{-1}$

NMR (CDCl$_3$, 200 MHz) δ3.60 (3H, s); 4.26 (1H, d, J=12.3 Hz); 4.41 (1H, d, J=12.3 Hz); 4.81 (1H, m); 5.18 (1H, d, J=1.6 Hz); 6.64 (1H, m); 7.3–7.5 (5H, m); 8.3 (1H, br s).

EXAMPLE 16

7α-Methoxy-2-spiro-[2'-(1', 1'-diphenylcyclopropyl)]-4'-tert -butyl-pyrrolo[3,4-c]cepham 1,1-dioxide (compound 63)

A solution of 3-azidomethyl-4-tert-butylcarbonyl-7α-methoxy-2-spiro-[2'-(1',1'-diphenylcyclopropyl)]-3-cephem 1,1-dioxide (130 mg) and triphenylphosphine (90 mg) in dichloromethane (5 ml) was let stand for 20 hours at room temperature. After removal of the solvent under reduced pressure, the residue was chromatographed (silica gel, EtOAc/n-hexane mixtures as eluants) furnishing the title product as a white powder (60 mg).

IR (KBr) ν$_{max}$ 3250–3500, 1765 cm$^{-1}$

NMR (CDCl$_3$, 200 MHz) δ1.37 (9H, s); 2.13 (1H, d, J=5.9 Hz); 2.80 (1H, d, J=5.9 Hz); 3.52 (3H, s); 4.72 (1H, d, J=1.4 Hz); 5.04 (1H, d, J=1.4 Hz); 5.11 (1H, d, J=3.1 Hz); 7.1–7.6 (11H, m).

EXAMPLE 17

7α-Methoxy-2-spiro-[2'-(1',1'-diphenylcyclopropyl)]-4'-tert -butyl-furo[3,4-c]cepham 1,1-dioxide (compound 30)

A solution of 3-bromomethyl-4-tert-butylcarbonyl-7α-methoxy-2-spiro-[2'-(1',1'-diphenylcyclopropyl)]-3-cephem 1,1-dioxide (200 mg) in acetone (15 ml) and water (5 ml) was treated with silver trifluoromethansulfonate (200 mg), which caused the formation of a white precipitate. After stirring for 15 min at room temperature, para-toluensulfonic acid (100 mg) was added and the resulting mixture was stirred for 90 min, then poured in EtOAc/water. The organic layer was washed with saturated aqueous NaHCO$_3$ and twice with brine, then dried (NA$_2$SO$_4$) and rotoevaporated. The residue was purified by silica gel chromatography (eluting with EtOAc/n-hexane mixtures) affording the title product as a white solid (110 mg).

IR (KBr) ν$_{max}$ 1770 cm$^{-1}$

EXAMPLE 18

6-(3,3-Dimethyl-2-oxo-butyl)-2-methoxy-3,3-dioxo-7-phenyl-2, 2a,4,6-tetrahydro-3-thia-6,7b-diaza-cyclobuta[e]inden-1-one (compound 98)

A solution of 7α-methoxy-4'-phenyl-pyrrolo [3,4-c] cepham 1,1-dioxide (63 mg) in acetonitrile (2 ml) was treated with 1-bromopinacolone (0.1 ml) and cesium carbonate (80 mg). The resulting mixture was stirred at room temperature overnight. After partitioning between EtOAc and water, the organic phase was dried (Na$_2$SO$_4$) and concentrated in vacuo. The residue was purified by flash chromatography (eluting with EtOAc/n-hexane mixtures) affording the title product as a light pink solid (55 mg).

IR (KBr) ν$_{max}$ 1775, 1720 cm$^{-1}$

NMR (CDCl$_3$, 200 MHz) δ0.05 (9H, s); 3.51 (3H, s); 4.25 (1H, d, J=16.1 Hz); 4.47 (1H, d, J=16.1 Hz); 4.52 (1H, d, J=18.2 Hz); 4.74 (1H, m); 4.82 (1H, d, J=18.2 Hz); 5.09 (1H, d, J=1.5 Hz); 6.43 (1H, s); 7.2–7.5 (5H, m).

EXAMPLE 19

Following a procedure similar to that described in Example 18 the following products were obtained:

2-Methoxy-6-(4-nitro-benzyl)-3,3-dioxo-7-phenyl-2,2a, 4,6-tetrahydro-3-thia-6,7b-diaza-cyclobuta [e]inden-1-one (compound 100)

IR (KBr) ν$_{max}$ 1780 cm$^{-1}$

NMR (CDCl$_3$, 200 MHz) δ3.53 (3H, s); 4.26 (1H, d, J=16.1 Hz); 4.42 (1H, d, J=16.1 Hz); 4.75 (1H, m); 5.00 (1H, d, J=17.0 Hz); 5.08 (1H, d, J=17.0 Hz); 5.10 (1H, d, J=1.4 Hz); 6.55 (1H, s); 7.0–8.2 (9H, m).

(2-Methoxy-1,3,3-trioxo-7-phenyl-1,2,2a,
4-tetrahydro-3-thia-6,7b-diaza-cyclobuta
[e]inden-6-yl)-acetic acid allyl ester (compound
108)

IR (KBr) $v_{max}$ 1780 cm$^{-1}$

NMR (CDCl$_3$, 200 MHz) δ3.52 (3H, s); 4.25 (1H, d, J=16.0 Hz); 4.42 (1H, d, J=16.0 Hz); 4.46 (1H, d, J=17.5 Hz); 4.54 (1H, d, J=17.5 Hz); 4.56 (2H, m); 4.73 (1H, m); 5.09 (1H, d, J=1.5 Hz); 5.1–5.3 (2H, m); 5.80 (1H, m); 6.56 (1H, s); 7.3–7.5 (5H, m).

4-(2-Methoxy-1,3,3-trioxo-7-phenyl-1,2,2a,
4-tetrahydro-3-th ia-6,7b-diaza-cyclobuta
[e]inden-6-ylmethyl)-benzoic acid allyl ester
(compound 123)

IR (KBr) $v_{max}$ 1780, 1710 cm$^{-1}$

EXAMPLE 20

(2-Methoxy-1,3,3-trioxo-7-phenyl-
1,2,2a,4-tetrahydro-3-thia-6,7b-diaza-cyclobuta[e]
inden-6-yl)-acetic acid sodium salt (compound 96)

(2-Methoxy-1,3,3-trioxo-7-phenyl-1,2,2a,4-tetrahydro-3-thia-6,7b-diaza-cyclobuta[e]inden-6-yl)-acetic acid allyl ester (60 mg) was dissolved in dichloromethane/tetrahydrofuran 1:1 (2ml) and sequentially treated with triphenylphosphine (5 mg), sodium 2-ethylhexanoate (20 mg) and tetrakistriphenylphosphine palladium(O) (5 mg). After stirring for 2 hours at room temperature, diisopropyl ether (10 ml) was added. The precipitate was purified by reverse phase chromatography (Li-Chroprep RP C-18, eluting with water then water/acetonitrile mixtures) allowing the isolation of the title product as a white powder (45 mg)

IR (KBr) $v_{max}$ 1780, 1610 cm$^{-1}$

EXAMPLE 21

4-(2-Methoxy-1,3,3-trioxo-7-phenyl-1,2,2a,4-
tetrahydro-3-th
ia-6,7b-diaza-cyclobuta[e]inden-6-ylmethyl)-benzoic
acid sodium salt (compound 119)

Obtained by a procedure similar to that described in Example 20

IR (KBr) $v_{max}$ 1760, 1595, 1550 cm$^{-1}$

Preparation 1

4-tert-Butylcarbonyl-3-hydroxymethyl-(7α)-
methoxy-(2α)-methyl-3-cephem 1,1-dioxide Step A: 4-tert-butylcarbonyl-(7α)-methoxy-2-methylene-3-methyl-3-cephem 1,1-dioxide A solution of 4-tert-butylcarbonyl-(7α)-methoxy-3-methyl-3-cephem 1,1-dioxide (1.2 g, 4 mmol) and N,N-dimethylmethylenimmonium chloride (0.8 g, 8.6 mmol) in dioxane (20 ml) and tert-butanol (6 ml) was heated at 90° C. for 15 hours. The mixture was partitioned between EtOAc and water, and the organic phase was repeatedly washed with water, then dried and concentrated. After treatment of the residue with ethyl ether, the title product was obtained as a white powder (1.19 g, 95% yield), mp 195°–196° C.

IR (KBr) $v_{max}$ 1780, 1698 cm$^{-1}$ $^1$H NMR (CDCl$_3$, 200 MHz): δ1.26 (9H,s), 1.81 (3H,s); 3.55 (3H,s), 4.77 (1H,d,J=1.8 Hz); 5.23 (1H,d,J=1.8 Hz); 5.91 (1H,d,J=2.0 Hz); 6.50 (1H,d,J=2.0 Hz).

Step B: 4-tert-Butylcarbonyl-(7α)-methoxy-(2α,3)-dimethyl-3- cephem 1,1-dioxide and 4-tert-butylcarbonyl-(7α)-methoxy(2β,3)dimethyl-3-cephem 1,1-dioxide A solution of the 2-methylene-cephem prepared in Step A (500 mg, 0.16 mmol) in EtOAc (45 ml) and EtOH (5 ml) was treated with 5% Palladium on CaCO$_3$ (500 mg) and hydrogenerated under pressure (4 atm.) at room temperature for 5 hours. The catalyst was removed by filtration and the filtrate was concentrated under vacuum. Following silica gel chromatography, two main products were isolated. The first eluted product was shown to be the 2α-methyl isomer (200 mg, 40% yield), mp 120°–123° C.

IR (KBr) $v_{max}$ 1770, 1695 cm$^{-1}$.

$^1$H NMR (CDCl$_3$, 200 MHz): δ1.24 (9H,s); 1.64 (3H,d, J=7.3 Hz); 1.71 (3H,s); 3.29 (1H,q,J=7.3 Hz); 3.53 (3H,s); 4.69 (1H,d,J=1.7 Hz); 5.16 (1H,d,J=1.7 Hz). The slower running product was the 2β-epimer (240 mg, 48% yield), mp 145°–146° C.

IR (KBr) $v^{max}$ 1790, 1698 cm$^{-1}$.

$^1$H NMR (CDCl$_3$, 200 MHz): δ1.24 (9H,s), 1.54 (3H,d, J=7.3 Hz); 1.63 (3H,d,J=1.0 Hz); 3.55 (3H,s); 3.82 (1H,m); 4.64 (1H,dd,J=1.5 and 1.6 Hz); 1.63 (1H,d,J=1.6 Hz).

Step C: 3-Bromomethyl-4-Tert-butylcarbonyl-(7α)-methoxy-2α-methyl-3-cephem 1,1-dioxide A solution of 4-tert-butylcarbonyl-(7α)-methoxy-(2α,3)-dimethyl-3-cephem 1,1-dioxide (150 mg) in CCl$_4$ (15 ml) was treated with N-bromosuccinimmide (85 mg) and a catalytic amount of azo-bis-isobutyronitrile (5 mg) then heated at reflux for 2.5 hours. After removal of the solvent the residue was purified by flash chromatography (SiO$_2$, eluting with EtOAc/cyclohexane mixtures), giving the title product as a yellowish foam (85 mg).

IR (CHCl$_3$) 1805, 1705 cm$^{-1}$ .

NMR (CDCl$_3$, 200 MHz): δ1.29 (9Hs); 1.75 (3H,d,J=7.4 Hz); 3.54 (3H,s); 3.74 (1H,q,J=7.4 Hz); 3.78 (1H,d,J=11.6 Hz); 3.92 (1H,d,J=11.6 Hz); 4.79 (1H,d,J=1.9 Hz); 5.18 (1H,d,J=1.9 Hz).

Step D: 4-tert-Butylcarbonyl-3-hydroxymethyl-(7α)-methoxy-(2α)-methyl-3-cephem 1,1-dioxide A solution of 3-bromomethyl-(7α)-methoxy-(2α)-methyl-3-cephem 1,1-dioxide (80 mg) in acetone (6 ml) and water (2 ml) was treated with silver triflate (60 mg). A white precipitate formed almost immediately. After stirring five minutes at room temperature the reaction mixture was poured into EtOAc and water. Following drying over Na$_2$SO$_4$ and evaporation of the solvent the crude title product was obtained as a yellowish foam (52 mg).

IR (CHCl$_3$) 1800, 1700 cm$^{-1}$.

Preparation 2

3-Bromomethyl-4-tert-butylcarbonyl-(7α)-
methoxy-(2β)-methyl-3-cephem 1,1-dioxide A solution of 4-tert-butylcarbonyl-(7α)-methoxy-(2β)-methyl-3-methyl-3-cephem 1,1-dioxide (see Preparation 1, Step B) (130 mg) in carbon tetrachloride (12 ml) was treated with N-bromosuccinimide (73 mg) and a catalytic amount of azo-bis-isobutyronitrile. After heating for 2 hours at reflux the mixture was concentrated in vacuo and the residue was chromatographed (silica gel; EtOAc/cyclohexane mixtures as eluants), affording the title product as a light yellow foam (95 mg).

IR (CHCl$_3$) 1805, 1700 cm$^{-1}$.

NMR (CDCl$_3$, 200 MHz): δ1.30 (9H,s); 1.61 (3H,d,J=7.2 Hz); 3.55 (3H,s); 3.87 (2H,s); 4.23 (1H,dq,J=1 and 7.2 Hz); 4.78 (1H,m); 5.22 (1H,d,J=1.7 Hz).

Preparation 3

3-Bromomethyl-(2α)-tert-butoxycarbonylmethyl-4-tert-butylcarbonyl-(7α)-methoxy-3-cephem 1,1-dioxide A mixture of (2α)-tert-butoxycarbonylmethyl-4-tert-butylcarbonyl-(7α)-methoxy-3-methyl-3-cephem 1,1-dioxide (350 mg), N-bromosuccinimide (190 mg) and azo-bis-isobutyronitrile (5 mg) in carbon tetrachloride (80 ml) and methylene chloride (5 ml) was heated at reflux for 2.5 hours. After cooling to room temperature, the reaction mixture was sequentially washed with aq. $NaHSO_3$, water then aq. $NaHCO_3$. The organic phase was dried ($Na_2SO_4$) then concentrated. Flash chromatography of the residue allowed the isolation of the title product as a waxy solid (200 mg).

IR (KBr) 1800, 1730, 1700 cm$^{-1}$.

NMR (CDCl$_3$, 200 MHz): δ1.28 (9H,s); 1.45 (9H,s); 3.03 (1H,dd,J=5.7 and 18.4 Hz); 3.24 (1H,dd,J=3.3 and 18.4 Hz); 3.54 (3H,s); 3.75 (1H,d,J=11.7 Hz); 3.92 (1H,m); 3.96 (1H,d,J=11.7 Hz); 5.16 (1H,d,J=1.8 Hz); 5.30 (1H,d,J=1.8 Hz). FD-MS: 493 (M$^+$).

Preparation 4

3-Acetylthiomethyl-4-tert-butylcarbonyl-(7α)-methoxy-3-cephem 1,1-dioxide

A solution of 3-bromomethyl-4-tert-butylcarbonyl-(7α)-methoxy-3-cephem 1,1-dioxide (190 mg) in acetonitrile (5 ml) was sequentially treated at 0° C. with thioacetic acid (107 μl) and triethylamine. The resulting solution was stirred for 30 minutes at room temperature, then poured into ethyl acetate/water. The upper phase was dried over $Na_2SO_4$ and concentrated under vacuum.

The residue was purified by flash chromatography eluting with cyclohexane ethyl acetate mixtures.

The title product was obtained as a white solid (180 mg).

IR (KBr) 1785, 1697 cm$^{-1}$.

NMR (CDCl$_3$, 200 MHz): δ1.25 (9H,s); 2.36 (3H,s); 3.41 (1H,d,J=14.4 Hz); 3.53 (1H,d,J=14.4 Hz); 3.54 (3H,s); 3.60 (1H,d,J=17.8 Hz); 3.94 (1H,dd,J=1.2 and 17.8 Hz); 4.67 (1H,m); 5.14 (1H,d,J=1.7 Hz). FD-MS: 375 (M$^+$).

Preparation 5

3-Azidomethyl-4-tert-butylcarbonyl-(7α)-methoxy-3-cephem 1,1-dioxide

A solution of 3-bromomethyl-4-tert-butylcarbonyl-(7α)-methoxy-3-cephem 1,1-dioxide (190 mg) in acetonitrile (20 ml) was treated with silver azide (150 mg).

After stirring for 2.5 hours at room temperature the reaction mixture was partitioned between EtOAc and water. The organic phase was dried over $Na_2SO_4$ and rotoevaporated to afford the title product as a yellowish solid (170 mg).

IR (KBr) 2120, 1770, 1700 cm$^{-1}$.

NMR (CDCl$_3$, 200 MHz): δ1.26 (9H,s); 3.55 (3H,s); 3.61 (1H,d,J=14.2 Hz); 3.67 (1H,d,J=17.9 Hz); 3.81 (1H,d,J=14.2 Hz); 4.00 (1H,dd,J=1.1 and 17.9 Hz); 4.74 (1H,m); 5.18 (1H,d,J=1.7 Hz).

Preparation 6

Following the method described under Preparation 5 the following products were obtained:

3-Azidomethyl-7α-methoxy-4-phenylcarbonyl-3-cephem 1,1-dioxide

IR (KBr) ν$_{max}$ 2110, 1780, 1715 cm$^{-1}$

NMR (CDCl$_3$, 200 MHz) δ3.52 (3H, s); 3.74 (1H, d, J=14.5 Hz); 3.82 (1H, d, J=18.0 Hz); 3.85 (1H, d, J=14.5 Hz); 4.07 (1H, dm, J=18.0 Hz); 4.87 (1H, m); 5.21 (1H, d, J=1.7 Hz); 7.5–8.0 (5H, m).

3-Azidomethyl-4-tert-butylcarbonyl-7α-methoxy-2-spiro-[2'-(1',1'-diphenylcyclopropyl)]-3-cephem 1,1-dioxide IR (KBr) ν$_{max}$ 2120, 1800, 1710 cm$^{-1}$ Preparation 7

Following the method described under Preparation 2 the following products were obtained:

3-Bromomethyl-7α-methoxy-4-(4-phenyl)phenylcarbonyl-3-cephem 1,1-dioxide

IR (KBr) ν$_{max}$ 1795, 1670 cm$^{-1}$

NMR (CDCl$_3$, 200 MHz) δ3.54 (3H, s); 3.82 (1H, d, J=11.3 Hz); 3.85 (1H, d, J=18 Hz); 3.97 (1H, d, J=11.3 Hz); 4.26 (1H, dm, J=18 Hz); 4.90 (1H, m); 5.24 (1H, d, J=1.9 Hz); 7.4–8.1 (9H, m).

3-Bromomethyl-4-tert-butylcarbonyl-7α-methoxy-2-spiro-[2'-(1',1'-diphenylcyclopropyl)]-3-cephem 1,1-dioxide IR (KBr) ν$_{max}$ 1790, 1690 cm$^{-1}$ NMR (CDCl$_3$, 200 MHz) δ1.33 (3H, s); 2.24 (1H, d, J=11.3 Hz); 2.49 (1H, d, J=7.7 Hz); 3.12 (1H, d, J=7.7 Hz); 3.17 (1H, d, J=11.3 Hz); 3.48 (2H, s); 4.98 (1H, d, J=2.1 Hz); 5.10 (1H, d, J=2.1 Hz); 7.2–7.6 (10H, m).

Preparation 8

3-Acetoxymethyl-4-tert-butylcarbonyl-7α-methoxy-2-(1-methyl-1,2,3,4-tetrazol-5-yl)thio-3-cephem 1,1-dioxide A solution of 3-acetoxymethyl-4-tert-butylcarbonyl-7α-methoxy-3-cephem 1,1-dioxide (1.05 g) in dichloromethane (100 ml) was sequentially treated with N-bromosuccinimide (575 mg) and triethylamine (0.4 ml). After stirring for 15 min at room temperature, the mixture was concentrated under reduced pressure (temperature of the bath <25° C.). Flash chromatography of the residue allowed the isolation of 3-acetoxymethyl-2-bromo-4-tert-butylcarbonyl-7α-methoxy-3-cephem 1,1-dioxide as a yellowish solid (850 mg). A portion of this material (130 mg) was dissolved in acetonitrile (10 ml) and treated with 2-mercapto-1-methyl-1,2,3,4-tetrazole sodium salt dihydrate (130 mg). The mixture was stirred at room temperature for 1 hour then poured into EtOAc/water. The upper layer was dried ($Na_2SO_4$) and concentrated. Purification of the residue by flash chromatography gave the title product as a white solid (105 mg).

IR (KBr) ν$_{max}$ 1805, 1750, 1705 cm$^{-1}$

NMR (CDCl$_3$, 200 MHz) δ1.26 (9H, s); 2.14 (3H, s); 3.57 (3H, s); 4.08 (3H,s); 4.32 (1H, d, J=13.2 Hz); 4.79 (1H, d, J=13.2 Hz); 5.15 (1H, d, J=2 Hz); 5.22 (1H, d, J=2 Hz); 5.35 (1H, s).

Preparation 9

Following a procedure similar to that described in Preparation 8 the following products were obtained:

3-Acetoxymethyl-4-tert-butylcarbonyl-2-(5-benzhydryloxy-2-methyl-5-oxo-2,5-dihydro-1,2,4-triazin-3-yl)thio-7α-methoxy-3-cephem 1,1-dioxide IR (KBr) ν$_{max}$ 1800, 1750, 1700 (sh), 1680 cm$^{-1}$ NMR (CDCl$_3$, 200 MHz) δ1.25 (9H, s); 2.12 (3H, s); 3.57 (3H, s); 3.66 (3H,s); 4.19 (1H, d, J=13.3 Hz); 4.76 (1H, d, J=13.3 Hz); 5.14 (1H, m); 5.23 (1H, d, J=2 Hz); 6.01 (1H, s); 6.74 (1H, s); 7.2–7.5 (10H, m).

3-Acetoxymethyl-2-
(5-benzhydryloxy-2-methyl-5-oxo-2,5-dihydro-
1,2,4-triazin-3-yl)thio-7α-methoxy-
4-phenylcarbonyl-3-cephem 1,1-dioxide IR (KBr) ν$_{max}$ 1800, 1750, 1680 cm$^{-1}$ NMR (CDCl$_3$, 200 MHz) δ1.97 (3H, s); 3.53 (3H, s); 3.69 (3H,s); 4.29 (1H, d, J=13.6 Hz); 4.71 (1H, d, J=13.6 Hz); 5.15 (1H, m); 5.25 (1H, d, J=2.1 Hz); 6.23 (1H, br s); 6.76 (1H, s); 7.2–8.0 (15H, m).

3-Acetoxymethyl-4-tert-butylcarbonyl-
7α-methoxy-2-(5-methyl-1,3,4-thiadiazol-2-yl)thio-
3-cephem 1,1-dioxide IR (KBr) ν$_{max}$ 1800, 1750, 1700 cm$^{-1}$ NMR (CDCl$_3$, 200 MHz) δ1.23 (9H, s); 2.12 (3H, s); 2.80 (3H, s); 3.57 (3H, s); 4.36 (1H, d, J=13.3 Hz); 4.77 (1H, d, J=13.3 Hz); 5.22 (1H, d, J=2.1 Hz); 5.31 (1H, d, J=2.1 Hz); 5.53 (1H, s).

3-Acetoxymethyl-7α-methoxy-2-(1-methyl-
1,2,3,4-tetrazol-5-yl)thio-4-phenylcarbonyl-3-cephem
1,1-dioxide IR (KBr) ν$_{max}$ 1800, 1750, 1680 cm$^{-1}$ NMR (CDCl$_3$, 200 MHz) δ1.96 (3H, s); 3.55 (3H, s); 4.09 (3H, s); 4.44 (1H, d, J=13.6 Hz); 4.80 (1H, d, J=13.6 Hz); 5.24 (1H, d, J=2 Hz); 5.26 (1H, d, J=2 Hz); 5.51 (1H, s); 7.4–8.0 (5H, m).

Preparation 10

3-Acetoxymethyl-4-tert-butylcarbonyl-
7α-methoxy-2-pivaloyloxy-3-cephem 1,1-dioxide 3-Acetoxymethyl-2-bromo-4-tert-butylcarbonyl-7α-methoxy-3-cephem 1,1-dioxide (350 mg) (prepared as described in Preparation 8) was dissolved in acetonitrile (10 ml) and treated with silver pivalate (220 mg). After stirring for 15 min at r.t. the reation mixture was filtered and the filtrate was rotoevaporated. Folowing flash chromatography of the residue, the title product was obtained as a white powder (250 mg).

IR (KBr) ν$_{max}$ 1805, 1760, 1705 cm$^{-1}$

NMR (CDCl$_3$, 200 MHz) δ1.27 (9H, s); 1.28 (9H, s); 2.06 (3H, s); 3.57 (3H, s); 4.29 (1H, d, J=13.3 Hz); 4.50 (1H, d, J=13.3 Hz); 4.73 (1H, d, J=2.1 Hz); 5.19 (1H, d, J=2.1 Hz); 5.99 (1H, s).

Preparation 11

3-Acetoxymethyl-4-tert-butylcarbonyl-
7α-methoxy-2-(β-naphthoyloxy)-3-cephem
1,1-dioxide.

The title product was obtained by a procedure similar to that described in preparation 10.

IR (KBr) ν$_{max}$ 1805, 1745, 1700 cm$^{-1}$

NMR (CDCl$_3$, 200 MHz) δ1.33 (9H, s) ; 1.88 (3H, s); 3.59 (3H, s); 4.45 (1H, d, J=13.5 Hz); 4.59 (1H, d, J=13.5 Hz); 5.00 (1H, d, J=2.1 Hz); 5.25 (1H, d, J=2.1 Hz); 6.22 (1H, s), 7.5–8.7 (7H, m).

We claim:

1. A compound of the formula (I),

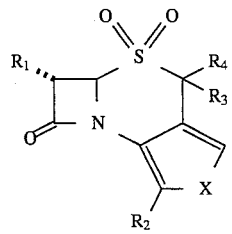

(I)

wherein R$_1$ is hydrogen or halogen or an optionally substituted C$_1$–C$_6$ alkyl, C$_2$–C$_6$ alkenyl, C$_1$–C$_6$ alkoxy, C$_1$–C$_6$ alkylthio, C$_1$–C$_6$ acyloxy or C$_1$–C$_6$ carboxamido group;

R$_2$ is hydrogen or an optionally substituted C$_1$–C$_6$ alkyl, C$_3$–C$_6$ cycloalkyl, C$_6$–C$_{10}$ aryl or C$_7$–C$_{14}$ aralkyl group;

R$_3$ is hydrogen or halogen or an optionally substituted C$_1$–C$_6$ alkyl, C$_3$–C$_6$ cycloalkyl, C$_7$–C$_{14}$ aralkyl group or an optionally substituted —(CH$_2$)$_m$S(O)$_n$R$_5$ group wherein m is 0 or 1, n is 0, 1 or 2 and R$_5$ is either a group defined as R$_2$ above or an optionally substituted heterocyclyl group; or a group of the formula OCOA, wherein A is hydrogen or an optionally substituted C$_1$–C$_{10}$ alkyl, C$_3$–C$_6$ cycloalkyl, C$_6$–C$_{10}$ aryl or C$_7$–C$_{14}$ aralkyl or heterocyclyl group, wherein said heterocyclyl group is selected from the group consisting of

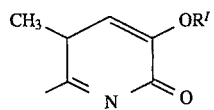
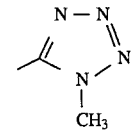
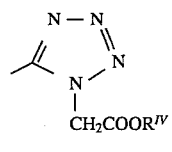
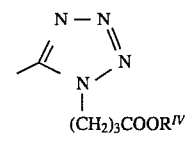
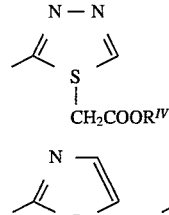
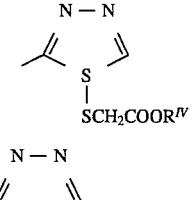
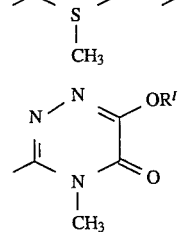

wherein R$'$ is hydrogen, methyl, ethyl, allyl, benzyl, or a hydroxy protecting group and R$^{IV}$ is hydrogen or methyl, ethyl, allyl, benzyl or a carboxy protecting group, R$_4$ is hydrogen or a group defined as R$_2$ above or R$_4$ taken together with R$_3$ constitutes a C$_2$–C$_6$ alkanediyl or an alkanediyl radical optionally substituted by methyl or phenyl, and X is oxygen, sulphur or NR$_6$, wherein R$_6$ is either hydrogen or a group as defined for R$_2$;

wherein said optional substituents are each independently selected from the group consisting of halogen; hydroxy; nitro; azido; amino; formyl; mercapto; cyano; carboxy($C_1$–$C_6$ alkyl); sulpho; $C_1$–$C_6$ acyl; trifluoroacetyl; $C_1$–$C_6$ carbamoyl; N-methylcarbamoyl; N-carboxymethylcarbamoyl; carbamoyloxy; $C_1$–$C_6$ acyloxy; $C_1$–$C_6$ alkoxycarbonyl; benzyloxycarbonyl; $C_1$–$C_6$ alkoxycarbonyloxy; benzyloxycarbonyloxy; $C_1$–$C_6$ alkoxy; phenoxy; benzyloxy; $C_1$–$C_6$ alkylthio; phenylthio; benzylthio; $C_1$–$C_6$ alkylsulphinyl; phenylsulphinyl; benzylsulphinyl; $C_1$–$C_6$ alkylsulphonyl, phenylsulphonyl; benzylsulphonyl; acylamino; sulphonamido; guanidino; $C_1$–$C_4$ alkyl; $C_2$–$C_4$ alkenyl; alkynyl; phenyl; $C_3$–$C_6$ cycloalkyl and methyl substituted with chloromethyl, fluoromethyl, difluoromethyl, trifluoromethyl, aminomethyl, dimethylaminomethyl, azidomethyl, cyanomethyl, carboxymethyl, sulphomethyl, carbamoylmethyl, (2-methyl-5-oxo-2,5-dihydro-5-hydroxy-1,2,4-triazin-3-yl)thiomethyl, carbamoyloxymethyl, hydroxymethyl, $C_1$–$C_4$ alkoxy carbonylmethyl, guanidinomethyl or carbamoyloxymethyl;

and pharmaceutically or veterinarily acceptable salts thereof and stereoisomers and tautomers thereof.

2. A compound according to claim 1 of the formula (I')

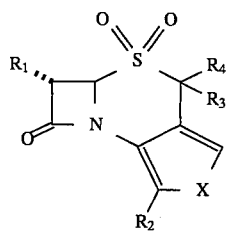 (I')

wherein $R_1$ is either hydrogen or a fluorine or chlorine atom; or methyl, ethyl, propyl, iso-propyl, n-butyl, 2-methyl-1-propyl, allyl, methallyl, crotyl, 3-methyl-2-buten-1yl, methoxy, ethoxy, propoxy, iso-propoxy, n-butoxy, methylthio, ethylthio, propylthio, isopropylthio, n-butylthio, formyloxy, acetoxy, propionyloxy, butyryloxy, formamido, acetamido, propionamido;

$R_2$ is hydrogen, or methyl, ethyl, propyl, iso-propyl, butyl, 2-methyl-1-propyl, neo-pentyl, 1,1-dimethylpropyl, vinyl, 1-propenyl, 2-methyl-1-propenyl, benzyl, cyclopropyl, cyclopentyl, cyclohexyl, phenyl, p-tert-butylphenyl, p-carboxyphenyl, p-sulphophenyl;

$R_3$ is either hydrogen or halogen or methyl, ethyl, methoxycarbonylmethyl, tert-butoxycarbonylmethyl, carboxymethyl, cyanomethyl, acetonyl, methoxymethyl, methoxyethoxymethyl, acetoxymethyl, benzyl, 4-methoxybenzyl, 4-nitrobenzyl or a —S(O)$_n$—Het group wherein n is 0, 1 or 2 and Het is a heterocyclic group selected from the following:

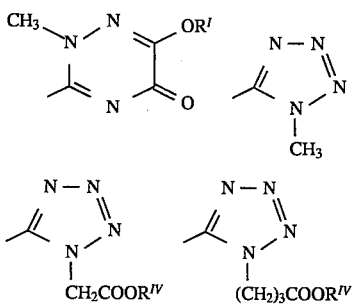

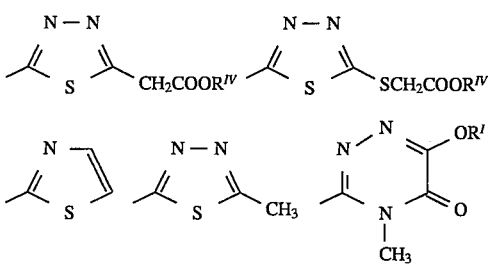

wherein $R^I$ is hydrogen, methyl, ethyl, allyl, benzyl, or a hydroxy protecting group and $R^{IV}$ is hydrogen or methyl, ethyl, allyl, benzyl, or a carboxy protecting group;

$R_4$ is methyl, ethyl, methallyl, crotyl, methoxycarbonylmethyl, tert-butoxycarbonylmethyl, carboxymethyl, cyanomethyl, acetonyl, methoxymethyl, methoxyethoxymethyl, acetoxymethyl, benzyl, 4-methoxybenzyl, 4-nitrobenzyl, benzhydryl, or a group

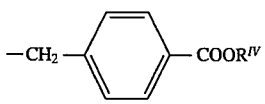

wherein $R^{IV}$ is as defined above;

or $R_4$ taken together with $R_3$ constitutes an ethylene (—CH$_2$CH$_2$—) or butylene (—CH$_2$CH$_2$CH$_2$CH$_2$—) radical, optionally substituted by one or two methyl or phenyl groups; and X is as defined in claim 1, and the pharmaceutical and veterinary acceptable salts thereof.

3. The compound of claim 1, which is of the formula (III)

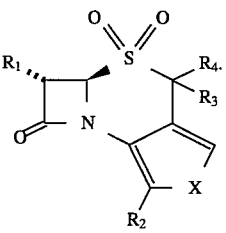 (III)

4. The compound of claim 1, wherein $R_1$ is halogen or an optionally substituted $C_1$–$C_6$ alkyl, $C_2$–$C_6$ alkenyl, $C_1$–$C_6$ alkoxy, $C_1$–$C_6$ alkylthio, $C_1$–$C_6$ acyloxy or $C_1$–$C_6$ carboxamido group.

5. The compound of claim 1, wherein $R_2$ is an optionally substituted $C_1$–$C_6$ alkylthio, $C_1$–$C_6$ alkyl, $C_3$–$C_6$ cycloalkyl, $C_6$–$C_{10}$ aryl or $C_7$–$C_{14}$ aralkyl group.

6. The compound of claim 1, wherein $R_3$ is halogen or an optionally substituted $C_1$–$C_6$ alkyl, $C_3$–$C_6$ cycloalkyl, $C_7$–$C_{14}$ aralkyl group or an optionally substituted —(CH$_2$)$_m$S(O)$_n$R$_5$ group wherein m is 0 or 1, n is 0, 1 or 2 and $R_5$ is either a group defined as $R_2$ above or an optionally substituted heterocyclyl group; or a group of the formula OCOA, wherein A is hydrogen or an optionally substituted $C_1$–$C_{10}$ alkyl, $C_3$–$C_6$ cycloalkyl, $C_6$–$C_{10}$ aryl or $C_7$–$C_{14}$ aralkyl or heterocyclyl group.

7. A composition comprising a pharmaceutically or veterinarily acceptable carrier and the compound according to claim 1.

8. A method for treating emphysema comprising administering a therapeutically acceptable amount of a compound according to claim 1.

9. The method of claim 8, wherein said mammal is human.

10. A process for preparing a compound of the formula (I)

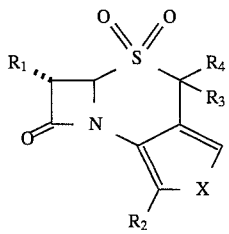

(I)

wherein $R_1$ is hydrogen or halogen or an optionally substituted $C_1$–$C_6$ alkyl, $C_2$–$C_6$ alkenyl, $C_1$–$C_6$ alkoxy, $C_1$–$C_6$ alkylthio, $C_1$–$C_6$ acyloxy or $C_1$–$C_6$ carboxamido group;

$R_2$ is an optionally substituted $C_1$–$C_6$ alkyl, $C_3$–$C_6$ cycloalkyl, $C_6$–$C_{10}$ aryl or $C_7$–$C_{14}$ aralkyl group;

$R_3$ is hydrogen or halogen or an optionally substituted $C_1$–$C_6$ alkyl, $C_3$–$C_6$ cycloalkyl, $C_7$–$C_{14}$ aralkyl group or an optionally substituted $-(CH_2)_mS(O)_nR_5$ group wherein m is 0 or 1, n is 0, 1 or 2 and $R_5$ is either a group defined as $R_2$ above or an optionally substituted heterocyclyl group; or a group of the formula OCOA, wherein A is hydrogen or an optionally substituted $C_1$–$C_{10}$ alkyl, $C_3$–$C_6$ cycloalkyl, $C_6$–$C_{10}$ aryl or $C_7$–$C_{14}$ aralkyl or heterocyclyl group, wherein said heterocyclyl group is selected from the group consisting of

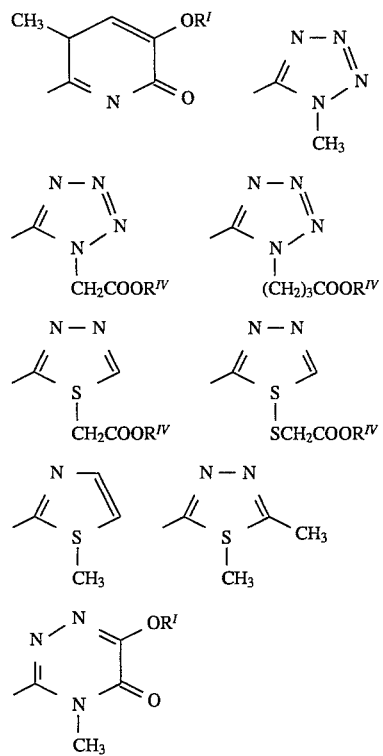

wherein $R'$ is hydrogen, methyl, ethyl, allyl, benzyl, or a hydroxy protecting group and $R^{IV}$ is hydrogen or methyl, ethyl, allyl, benzyl or a carboxy protecting group;

$R_4$ is hydrogen or a group defined as $R_2$ above or $R_4$ taken together with $R_3$ constitutes a $C_2$–$C_6$ alkanediyl or an alkanediyl radical optionally substituted by methyl or phenyl, and X is either oxygen or sulphur or $NR_6$, wherein $R_6$ is either hydrogen or a group as defined for $R_2$;

wherein said optional substituents are each independently selected from the group consisting of halogen; hydroxy; nitro; azido; amino; formyl; mercapto; cyano; carboxy($C_1$–$C_6$ alkyl); sulpho; $C_1$–$C_6$ acyl; trifluoroacetyl; $C_1$–$C_6$ carbamoyl; N-methylcarbamoyl; N-carboxymethylcarbamoyl; carbamoyloxy; $C_1$–$C_6$ acyloxy; $C_1$–$C_6$ alkoxycarbonyl; benzyloxycarbonyl; $C_1$–$C_6$ alkoxycarbonyloxy; benzyloxycarbonyloxy; $C_1$–$C_6$ alkoxy; phenoxy; benzyloxy; $C_1$–$C_6$ alkylthio; phenylthio; benzylthio; $C_1$–$C_6$ alkylsulphinyl; phenylsulphinyl; benzylsulphinyl; $C_1$–$C_6$ alkylsulphonyl, phenylsulphonyl; benzylsulphonyl; acylamino; sulphonamido; guanidino; $C_1$–$C_4$ alkyl; $C_2$–$C_4$ alkenyl; alkynyl; phenyl; $C_3$–$C_6$ cycloalkyl and methyl substituted with chloromethyl, fluoromethyl, difluoromethyl, trifluoromethyl, aminomethyl, dimethylaminomethyl, azidomethyl, cyanomethyl, carboxymethyl, sulphomethyl, carbamoylmethyl, (2-methyl-5-oxo-2,5-dihydro-5-hydroxy-1,2,4-triazin-3-yl)thiomethyl, carbamoyloxymethyl, hydroxymethyl, $C_1$–$C_4$ alkoxy carbonylmethyl, guanidinomethyl or carbamoyloxymethyl;

and pharmaceutically or veterinarily acceptable salts thereof and stereoisomers and tautomers thereof;

which process comprises:

(i) cyclizing a compound of the formula (II)

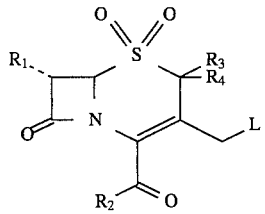

wherein $R_1$–$R_4$ are described above; and L is either a group XH, wherein X is oxygen, sulphur or $NR_6$, or a leaving group selected from the group consisting of halogen atoms; $C_{1-4}$ acyloxy; alkane- or arene-sulphonyloxy;

in a solvent at a temperature from –20° C. to 110° in the presence or absence of catalyst; and (ii) if desired, salifying the resulting compound of formula (I) into a pharmaceutically or a veterinarily acceptable salt thereof.

11. The process of claim 10, wherein said solvent in step (ii) is aqueous, organic or a thereof.

12. The process of claim 11, wherein said catalyst in step (ii) is an acid or base catalyst.

* * * * *